US00PP10003P

United States Patent [19]

Meilland

[11] Patent Number: Plant 10,003

[45] Date of Patent: Aug. 19, 1997

[54] HYBRID TEA ROSE PLANT NAMED 'MEIBICMARJ'

[75] Inventor: Alain A. Meilland, Antibes, France

[73] Assignee: The Conard-Pyle Company, West Grove, Pa.

[21] Appl. No.: 663,789

[22] Filed: Jun. 14, 1996

[51] Int. Cl.[6] ..... A01H 5/00

[52] U.S. Cl. ..... Plt./11

[58] Field of Search ..... Plt./11, 18, 19

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive long-lasting bicolored blossoms that are a blend of cream and pink. The floral buds are large. The floral stems are strong, very long, and erect. The plant exhibits an erect growth habit and strong vegetation. The new variety exhibits good disease resistance, including resistance to powdery mildew and botrytis, and is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Jelfarlay' variety (non-patented in the United States). The male parent (i.e., the pollen parent) was the product of the cross of the 'Meikola' variety (U.S. Plant Pat. No. 5,607) and the 'Korflug' variety (U.S. Plant Pat. No. 5,575). The parentage of the new variety can be summarized as follows:

'Jelfarlay'×('Meikola'×'Korflug').

The seeds resulting from the above pollination were sown and small plants were obtained which were physically and biologically different from each other. Selective study resulted in the identification of a single plant of the new variety.

It was found that the new variety of Hybrid Tea rose plant of the present invention possesses the following combination of characteristics:

(a) forms in abundance attractive bicolored blossoms that are a blend of cream and pink,
(b) exhibits an erect growth habit,
(c) is well suited for cut flower production under greenhouse growing conditions, and
(d) exhibits good disease resistance.

The floral buds of the new variety are large. The floral stems are strong, very long, and erect. Accordingly, the new variety well meets the needs of the horticultural industry and is particularly well suited for the commercial production of cut flowers while growing indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Meibicmarj' variety, and is being marketed under the ELEGANCE trademark.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obverse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of a flowering stem;

FIG. 13—illustrates a specimen of a main branch;

FIG. 14—illustrates a specimen of a leaf with three leaflets—plan view—upper surface.

FIG. 15—illustrates a specimen of a leaf with five leaflets—plan view—under surface; and FIG. 16—illustrates a specimen of a leaf with seven leaflets—plan view—upper surface.

DETAILED DESCRIPTION

Figures 1, 2, 3, 4, 5, 6, 7, 8, 9, 10, 11, 12, 13, 14, 15, 16:
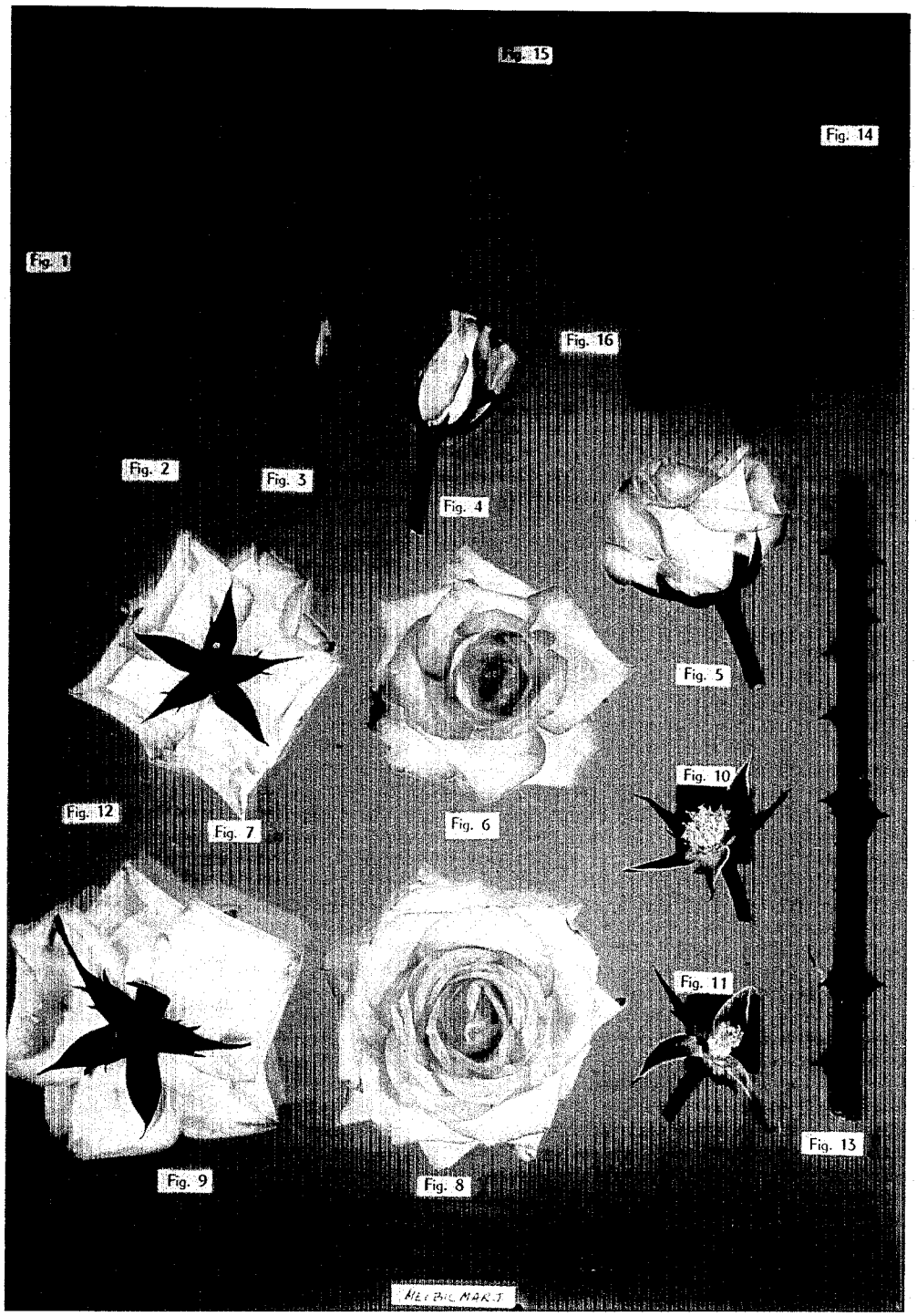

The chart used in the identification of the colors is that of the The Royal Horticultural Society (R.H.S. Colour Chart). The description is based on the observation during November of two-year-old plants while budded on *Rosa indica* understock and growing in greenhouses at Le Cannet des Maures, Var, France. The coloration in common terms precedes reference to the chart.

Class: Hybrid Tea.

Plant:

*Height.*—When pruned to a height of approximately 0.85 m., floral stems of approximately 70 to 100 cm. in length commonly are formed.

*Habit.*—Erect.

Branches:

*Color.*—Young stems: light green, Green Group 139C. Adult wood: medium green, Green Group 137D.

*Thorns.*—Size: medium. Quantity: moderately numerous (as illustrated). Color: greenish-reddish on young stems and greenish changing to tan on adult wood (as illustrated).

Leaves:

*Stipules.*—Adnate, pectinate, narrow and linear.

*Petioles.*—Upper surface: striped reddish brown on young foliage and medium green on adult foliage. Under surface: light green and commonly bear some small thorns.

*Leaflets.*—Number: commonly 3, 5 (most often), and 7. Shape: oval. Serration: single and regular. Texture: consistent. General appearance: dense, dark green in coloration, and semi-glossy. Color (young foliage): Upper surface: Bronze Green, Yellow-Green Group 146A, and suffused with reddish-brown coloration. Under surface: near Yellow-Green Group 146A and, suffused with reddish brown. Color (adult foliage): Upper surface: medium green, Green Group 139A. Under surface: light green, Greyed-Green Group 191A.

Inflorescence:

*Number of flowers.*—Usually one flower per stem.

*Peduncle.*—Light green in coloration and smooth. The length is approximately 13 to 15 cm. on average.

*Sepals.*—Upper surface: tomentose, and greenish in coloration. Under surface: light green in coloration and commonly with a few extensions.

*Buds*—Shape: conical. Length: approximately 4 to 5 cm. on average. Size: large. Color upon opening: Upper surface: Green-White Group 157A, edged with Red Group 42D. Under surface: Green-White Group 157B, edged with Red Group 42D.

*Flower.*—Shape: cup-shaped with a high center. Diameter: approximately 13 to 15 cm. on average. Color (when opening begins): Upper surface: Cream, Orange-White Group 159C, and lightly suffused with Red Group 48A on the marginal zone and edged with Red Group 48A. Under surface: Cream, Orange-White Group 159C, and edged with Red Group 48A. Color (when blooming): Upper surface: Cream, Orange-White Group 159C, lightly suffused with Red Group 48B, and edged with Red Group 48A. Under surface: Cream, Orange-White Group 159C, and edged with Red Group 48A. Color (at end of opening): Upper surface: light red, Red Group 49D, and edged with Red Group 51C. Under surface: Cream, Orange-White Group 159D, and edged with Red Group 51D. Fragrance: none. Lasting quality: very good. The blossoms commonly last approximately 7 to 9 days on the plant, and approximately 8 to 10 days when cut and placed in vase. Such blossom life is influenced by the environmental conditions that are encountered. Petal shape: generally rounded with reflexed edges. Petal number: approximately 40 to 45 on average. Stamen number: 88 to 93 on average. Anthers: normal, and ochre in coloration. Filaments: canary yellow in coloration. Pistils: approximately 80 to 85 on average. Stigmas: ochre in coloration. Styles: pinkish in coloration. Receptacle: light green in coloration, smooth, and in longitudinal section in the shape of a funnel.

Development:

*Vegetation.*—Strong.

*Blooming productivity.*—approximately 120 to 150 flowers per $m.^2$ per year.

*Resistance to diseases.*—Good, with good resistance being exhibited to botrytis and powdery mildew.

I claim:

1. A new and distinct variety of Hybrid Tea rose plant characterized by the following combination of characteristics:

(a) forms in abundance attractive bicolored blossoms that are a blend of cream and pink,
(b) exhibits an erect growth habit,
(c) is well suited for cut flower production under greenhouse growing conditions, and
(d) exhibits good disease resistance;

substantially as herein shown and described.

* * * * *